United States Patent [19]

Dewasmes

[11] Patent Number: 5,503,019
[45] Date of Patent: Apr. 2, 1996

[54] METHOD AND APPARATUS FOR ULTRASONICALLY INSPECTING THE SURFACE OF THE BORE OF A RAILROAD WHEEL AXLE

[75] Inventor: Raymond Dewasmes, Teteghem, France

[73] Assignee: Valdunes, Puteaux, France

[21] Appl. No.: 905,812

[22] Filed: Jun. 29, 1992

[30]   Foreign Application Priority Data

Jun. 28, 1991 [FR]   France ................................ 91 08094

[51] Int. Cl.[6] .................................................. G01N 29/04
[52] U.S. Cl. ............................................. 73/623; 73/629
[58] Field of Search ......................... 73/622, 634, 623, 73/620, 627, 629, 637, 638, 639

[56]           References Cited

U.S. PATENT DOCUMENTS 4,092,868  6/1978  Thompson et al. ..................... 73/638
4,162,635  7/1979  Triplett et al. ........................ 73/623
4,218,923  8/1980  Triplett et al. ........................ 73/623
4,306,459  12/1981 Johnson et al. ....................... 73/623
4,619,143  10/1986 Franken ................................ 73/623

Primary Examiner—Richard Chilcot
Assistant Examiner—Joseph L. Felber
Attorney, Agent, or Firm—Oblon, Spivak, McClelland, Maier & Neustadt

[57]              ABSTRACT

A method for ultrasonically inspecting the surface of a bore, particularly the bore of a railroad wheel axle, includes the step of generating a transverse ultrasonic wave from an emitter which interacts with the surface of the bore, and comparing the amplitude of the echoes obtained with values obtained from a calibration curve plotted for a bore having a standard defect which corresponds to the bore to be inspected so as to determine the existance of a defect when the amplitude of the echoes is greater than a specified fraction of the value indicated by the calibration curve. A corresponding device is provided for ultrasonically inspecting the surface of the bore of the railroad wheel axle.

4 Claims, 2 Drawing Sheets

METHOD AND APPARATUS FOR ULTRASONICALLY INSPECTING THE SURFACE OF THE BORE OF A RAILROAD WHEEL AXLE

BACKGROUND OF THE INVENTION

1. Field of the Invention

The present invention relates to a method and a device using ultrasound for inspecting the surface state of a bore, especially the bore of a railroad wheel axle.

2. Discussion of the Background

Railroad wheel axles are long parts of revolution, in which an axial bore is machined, over their entire length, by drilling. The surface of the bore is inspected so as to check that it doesn't include any defects, such as a tool blow, running the risk of decreasing the fatigue strength of the wheel axle. For this purpose, it has been proposed to carry out roughness measurements. However, these measurements can only be carried out in the vicinity of the ends of the wheel axle. It is also known to carry out an inspection using ultrasonics from outside the wheel axle. However, this method does not enable the complete bore to be inspected. In fact, the wheel axle includes several cylindrical portions connected by connection fillets. In the zones located in the vicinity of these connection fillets, it is not possible to carry out an inspection using ultrasonics from outside. Furthermore, this method is lengthy as it is necessary to scan the entire surface of the axle.

SUMMARY OF THE INVENTION

The object of the invention is therefore to produce a method and a device which enable the surface of a bore as a whole to be inspected easily and quickly.

The inspection method, which is the aim of the invention, is characterized by the following operations:

- with the aid of a suitably oriented emitter of longitudinal ultrasonic waves, of adapted frequency and which interacts with the surfaces of the bore, a transverse surface wave is generated on this surface,
- the amplitude of the echoes obtained is compared with the values from a calibration curve plotted for a bore which is provided with a standard defect and is identical to the bore to be inspected, and
- it is determined that there is a defect when the amplitude of an echo is greater than a specified fraction of the value indicated by the calibration curve.

The device for the implementation of this method comprises a sensor unit, provided with an orientable emitter-receiver probe, and a support in which a housing, adapted for receiving the sensor unit, is made, which sensor unit together with its support have a surface conjugate with the internal surface of the bore to be inspected so as to be able to interact with said internal surface.

According to one embodiment of this device, the support includes a portion slidably mounted on rods for connection with a base, these rods being provided with elastic means tending to move said portion and the base away from each other, the housing of the sensor unit being made in said portion, on which the surface conjugate with the interior surface of the bore is arranged.

Thus, in order to insert this sensor unit inside the bore to be inspected, the two constituent portions of the support are moved towards each other against the return force of the elastic means, which then moves the base and the portion sliding on the connecting rods away from each other, thereby applying these two parts against the internal surface of the bore.

BRIEF DESCRIPTION OF THE DRAWINGS

Other particular features and advantages of the invention will emerge in the course of the description which follows, made with reference to the attached drawings which illustrate, by way of non-limiting example, one embodiment thereof.

DESCRIPTION OF THE PREFERRED EMBODIMENT

Figure 1:
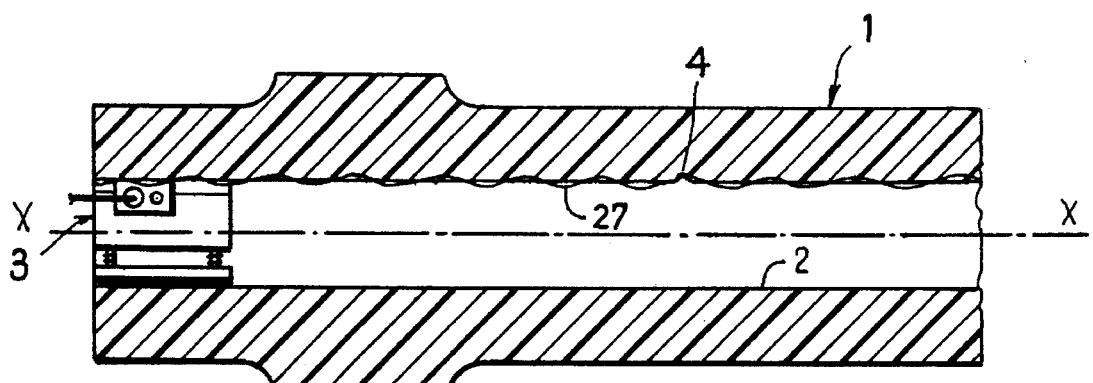
FIG. 1 is a view, in axial longitudinal cross section, of a railroad wheel axle, in the bore of which is placed an inspection device in accordance with the invention.
Figure 2:
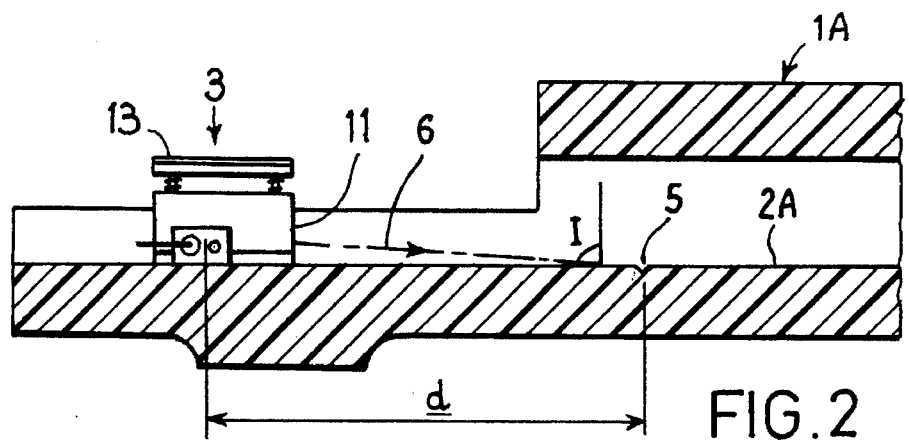
FIG. 2 is a view, in axial longitudinal cross section, of a reference axle serving to plot a calibration curve for the inspection device.
Figure 3:
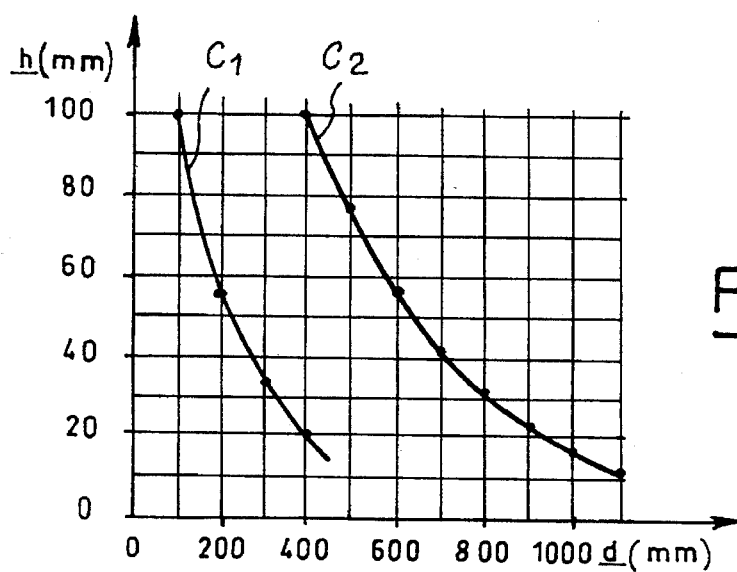
FIG. 3 is an example of calibration curves for the inspection device according to the invention.

The inspection method, which is the aim of the invention, will first of all be described with reference to FIGS. 1 to 3.

A railroad wheel axle 1 has a drilled axial bore 2, the surface state of which it is desired to inspect. In order to do this, a device 3 which can emit and receive ultrasonic signals is inserted into the bore 2 at one of its ends. The device 3 is connected to known, but not shown, means for generating pulses, for receiving and displaying signals. By suitably orienting the angle of incidence of the emitted ultrasonics with respect to the surface 2, the longitudinal waves which are able to propagate in the wheel axle 1 are made to disappear and only a surface wave 27, called a Rayleigh wave, remains which propagates at the surface of the bore 2, this wave 27 being represented symbolically by a wavy line in FIG. 1.

If such a wave 27 encounters a sufficiently large defect 4, it is partially reflected from this defect. The reflected wave returns as far as the device 3 where it is detected in a conventional manner. This detection is displayed by a display means which, also in a conventional manner enables the amplitude of the echo and the position of the defect 4 on the surface of the bore 2 to be determined. By making the device 3 rotate about the axis XX of the bore 2, it is thereby possible to inspect the surface of the bore at least as far as mid-length, and this is carried out without moving the device 3 longitudinally along the entire length of the bore 2. By then placing the device 3 at the other end of the axle 1, it is possible to inspect the second half of the bore 2 and, consequently, the complete surface of the bore 2 in two operations.

In order to carry out this inspection, it is necessary beforehand to adjust and calibrate the device 3. For this purpose, an wheel axle 1A is used which has the same geometry, the same chemical composition and which has undergone the same thermal treatment as the wheel axles to be inspected (FIG. 2). The wheel axle 1A is partially opened and a standard defect 5 is created on the surface of the bore 2A approximately halfway between the two ends of the wheel axle 1A.

The standard defect 5 can, preferably, be a parallel-face, flat-bottom notch having, for example, a width of 1 mm and a depth of 1 mm. The standard defect 5 can also be a V-shaped notch with, for example, an apex angle of 60° and a depth of 0.3 mm.

The standard defect 5 is produced after a preparation of the surface of the bore 2A by known means, the surface obtained having a roughness which is characterized by a specified coefficient Ra, for example Ra less than or equal to 3.2 (Ra being the arithmetical mean roughness coefficient).

The device 3 emits an ultrasonic beam 6 which makes an angle of incidence I normal to the surface of the bore 2A. The adjustment of this angle of incidence I is performed by positioning the device 3 on the surface of the bore 2A along the generatrix passing through the standard defect 5. The device 3 then emits ultrasonic pulses and the orientation of the ultrasound emitter is adjusted so that the amplitude of the echo sent back by the standard defect 5 is a maximum. Once the adjustment of angle of incidence has been carried out, the next step is the calibration of the device 3 by moving the latter along the generatrix and by recording the amplitude of the echo sent back by the standard defect, as a function of the distance d between the latter and the device 3. The calibration curves, such as the curves C1 and C2 of FIG. 3, in which the ordinates h represent the amplitude of the echo as a function of the distance d, are thus established.

During the inspection of a bore 2, the amplitude of the echoes and the distance d between the device 3 and the detected defect are measured and this amplitude is compared with that supplied by the calibration curve C. If the measured amplitude is, for example, half of that indicated by the curve it is possible to consider that there is no defect or that the defect is acceptable. If the opposite is the case, an examination in the vicinity of the detected defect is performed in minute detail.

By way of non-limiting indicative numerical example, for a steel axle 1, the frequency of the best adapted longitudinal ultrasonic wave 27 is 2 MHz and the optimum angle of incidence I is approximately 82°.

Figure 4:
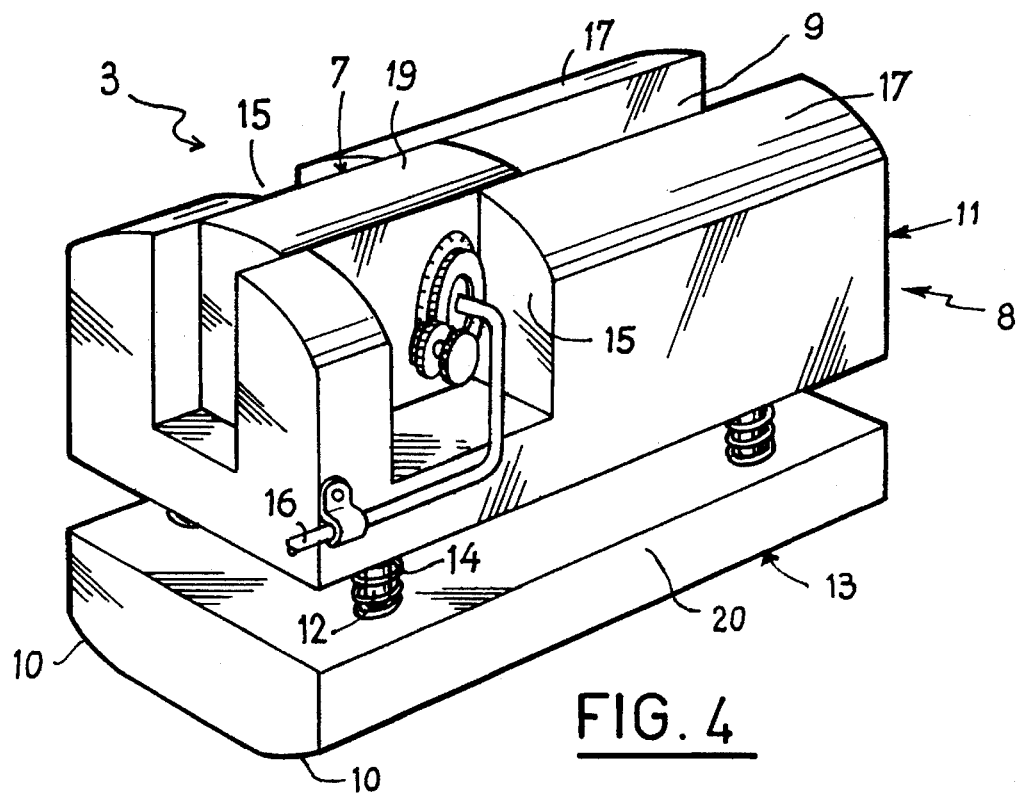
FIG. 4 is a perspective view of one embodiment of the inspection device using ultrasonics according to the invention.
Figure 5:
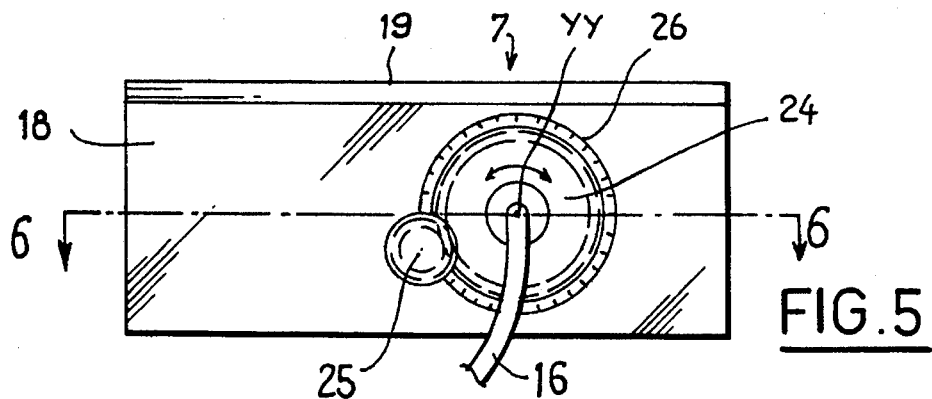
FIG. 5 is a view, in longitudinal elevation and on an enlarged scale, of the sensor unit of FIG. 4.
Figure 6:
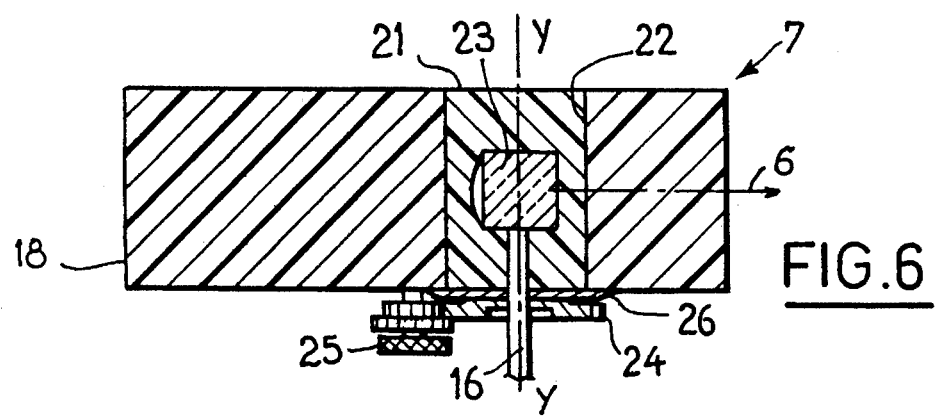
FIG. 6 is a view, in axial cross section, of the sensor unit along 6/6 of FIG. 5.

One embodiment of the device 3 for implementing the method which has just been described is shown in FIGS. 4 to 6.

This device 3 comprises a sensor unit 7 an ultrasonic emitter-receiver, and a support 8 in which a housing, adapted for receiving the sensor unit 7, is made. The support 8 includes a portion 11 mounted so as to slide on rods 12 for connection to a base 13, these rods 12 being, for example, four in number, as shown. They can be fixed to the base 13 and can slide in corresponding holes (not visible in the drawings) made inside the portion 11, or, conversely, the rods 12 can be fixed to the portion 11 and can slide in complementary holes formed in the base 11.

Elastic means, constituted for example by helical springs 14 coaxial with the rods 12 and compressed between the base 13 and the portion 11, tend to move these two parts away from each other.

In the example described, the portion 11 and the base 13 have an approximately parallelepipedal elongate shape. The housing 9 extends longitudinally from one end to the other of the sliding portion 11 (assuming that the rods 12 are fixed to the base 13 and that the portion 11 therefore slides on the rods 12). The housing 9 thus forms a longitudinal groove in the sliding portion 11 and is advantageously completed by two lateral undercuts formed in the portion 11 on each side of the groove 9 in order to permit the installation of the sensor unit 7. In fact, the latter is connected to the pulse-generation, detection and display means (not shown) via a lead 16 which passes through one of the undercuts 15.

On either side of the longitudinal housing 9, the surface of the portion 11, on the opposite side from the base 13, is conjugate with the internal cylindrical surface of the bore 2 to be inspected, so as to be able to interact with this surface. The two surfaces 17 are mutually symmetrical with respect to the longitudinal housing 9 and are therefore cylinder portions having the same radius of curvature as the bore 2.

The face of the base 13 on the opposite side from the cylindrical surfaces 17 and 19 also has cylindrical fillets 10 for connection to its plane lateral faces 20; the fillets 10 therefore constitute portions of cylindrical surfaces of the same radius of curvature as the bore 2 and as the opposite surfaces 17, 19, so as to be able to be applied, like this surface, to the surface of the bore 2.

The sensor unit 7 includes (FIG. 5 and 6) a first part 18 whose lateral surface 19 is profiled so as to be complementary with the surfaces 17 of the support 8. In other words, the height of the part 18 being equal to the depth of the housing 9 and the lateral surface 19, having the same radius of curvature as the surfaces 17, is flush with the latter so that the surfaces 17 and 19 can be applied against the cylindrical surface of the bore 2 to be inspected.

The sensor unit 7 comprises a cylindrical second part 21 mounted so as to rotate about an axis YY in a cylindrical hole 22 formed in the first part 18, and an ultrasound emitter-receiver 23 is embedded inside the part 21, this probe 23 being connected to the leads 16. The part 21 is produced from an appropriate synthetic material in a known manner. The rotation axis YY of the cylindrical part 21 is perpendicular to the longitudinal axis of the housing 9 and, consequently, to the axis XX of the bore 2 to be inspected.

The sensor unit 7 is equipped with means for adjusting the angular position of the cylindrical part 21 about its rotation axis YY which, in the example shown, are formed in the following manner: a gearing 24 is fixed to one of the front faces of the cylindrical part 21, coaxially with the axis YY, and is pierced through at its center by a hole for passage of the lead 16. A knurled knob 25 is mounted on the lateral face of the part 18 and positioned so as to be able to interact with the toothing of the gearing 24, the angular position of which can be referenced by any appropriate means, for example a vernier 26 mounted on the part 18. Thus the rotation of the knurled control knob 25 drives the toothing 24 and the cylindrical part 21 about the axis YY, which enables the ultrasonic beam 6 to be oriented into the desired direction inside the housing 9 and the bore 2. The rotation of the cylinder 21 enables the angle of incidence I of the ultrasonic beam 6 to be adjusted, the optimum position of the emitter-receiver 23 being referenced with the aid of the vernier 26.

The operation of the inspection device 3 which has just been described is carried out in the following manner.

Before inspecting a bore 2, the operator installs the device in the bore 2A of a calibration axle 1A and then the operator orients the emitter-receiver probe 23 about its rotation axis YY by acting on the control knob 25, as explained hereinabove. This maneuver enables the angle of incidence I of the ultrasonic beam 6, generating the transverse surface wave 27 at the surface of the bore 2A, to be adjusted.

After having adjusted the orientation of the emitter-receiver probe, the operator plots the calibration curve as indicated hereinabove.

In order to inspect a bore 2, first of all, by pressure on the base 13 and on the portion 11, the operator moves these two elements closer together, so as to be able to insert the whole device 3 inside the bore 2 to be inspected.

As soon as the pressure exerted on the base 13 and the portion 11 against the return force of the springs 14 is released, the latter move the two parts away from each other and firmly apply the surfaces 17, 19 and 10 against the surface of the bore 2, the device 3 thus being fixed in position in the bore to be inspected.

If a defect such as defect 4 exists in the inspected surface, the amplitude of the echos obtained is compared with the reference values of the calibration curve C, as explained hereinabove in the scope of the method in accordance with the invention.

By way of numerical indication, the emitter-receiver probe 23 can have a 10 mm diameter.

Obviously, numerous modifications and variations of the present invention are possible in light of the above teachings. It is therefore to be understood that, within the scope of the appended claims, the invention may be practiced otherwise than as specifically described herein.

I claim:

1. A method for ultrasonically inspecting the surface of a bore of a railroad axle, which comprises:

generating a transverse-ultrasonic wave from an emitter which interacts with the surface of the bore, comparing the amplitude of echoes of the wave obtained with values obtained from a calibration curve plotted for a bore having a standard defect that corresponds to the bore to be inspected so as to determine the existence of a defect in the bore tested when the amplitudes of the echoes are greater than a specified fraction of the value indicated by the calibration curve.

2. A method according to claim 1, which comprises obtaining the optimum orientation of the emitter by orienting said emitter until an echo of maximum amplitude is obtained from the standard defect.

3. A device for ultrasonically inspecting the surface of a bore of a railroad wheel axle, which comprises:

a sensor unit provided with an orientable ultrasonic emitter-receiver and a support having a longitudinal housing with a longitudinal axis, said housing slidably receiving the sensor unit therein, said support including a portion receiving the sensor unit, a base and elastic members which interconnect the portion receiving the sensor unit and the base, said elastic member moving said portion and the base away from each other and wherein said portion has lateral surfaces located in proximity with an interior surface of said bore;

the sensor unit including lateral surfaces positioned in proximity with an internal surface of the bore to be inspected so as to interact with said internal surface of said bore;

the sensor unit including a first part having a lateral surface profiled so as to be complementary to said lateral surfaces of the support, a second part rotatably mounted in the first part about an axis perpendicular to said longitudinal axis and which contains said ultrasonic emitter receiver and an adjusting mechanism, the adjusting mechanism adjusting the angular position of the second part about axis perpendicular to said longitudinal axis;

wherein the housing of the sensor unit extends from one end to an opposite end of said portion of the support for receiving the sensor unit, thereby forming a longitudinal groove emerging at the bore to be inspected;

wherein the face of the base opposite the portion of the support receiving the sensor unit has fillets integrally connected to lateral faces of the base and which are located in proximity with the surface of the bore to be inspected so as to be positioned against the surface of the bore.

4. A device for ultrasonically inspecting the surface of a bore of a railroad wheel axle, which comprises:

a sensor unit provided with an orientable ultrasonic emitter-receiver and a support having a longitudinal housing with a longitudinal axis, said housing slidably receiving the sensor unit therein, said support including a portion receiving the sensor unit, a base and elastic members which interconnect the portion receiving the sensor unit and the base, said elastic member moving said portion and the base away from each other and wherein said portion has lateral surfaces located in proximity with an internal surface of said bore;

the sensor unit including lateral surfaces positioned in proximity with said internal surface of the bore to be inspected so as to interact with said internal surface of said bore;

the sensor unit including a first part having a lateral surface profiled so as to be complementary to said lateral surfaces of the support, a second part rotatably mounted in the first part about an axis perpendicular to said longitudinal axis and which contains said ultrasonic emitter receiver and an adjusting mechanism, the adjusting mechanism adjusting the angular position of the second part about axis perpendiculator to said longitudinal axis;

wherein the housing of the sensor unit extends from one end to an opposite end of said portion of the support for receiving the sensor unit, thereby forming a longitudinal groove emerging at the bore to be inspected;

wherein the adjusting mechanism comprises a gearing attached to the second part and a control knob interacting with said gearing and which is mounted on said first part; and wherein the face of the base opposite the portion of the support receiving the sensor unit has fillets integrally connected to lateral faces of the base and which are located in proximity with the surface of the bore to be inspected so as to be able to be positioned against the surface of the bore.

* * * * *